US00PP35402P2

(12) United States Plant Patent
Smith

(10) Patent No.: US PP35,402 P2
(45) Date of Patent: Sep. 26, 2023

(54) ***CHRYSANTHEMUM* PLANT NAMED 'CIFZ0107'**

(50) Latin Name: ***Chrysanthemum* x *morifolium***
Varietal Denomination: CIFZ0107

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/110,031

(22) Filed: Feb. 15, 2023

(51) Int. Cl.
*A01H 5/02* (2018.01)
*A01H 6/14* (2018.01)

(52) U.S. Cl.
USPC ..... Plt./289
CPC ..... *A01H 6/1424* (2018.05)

(58) Field of Classification Search
USPC ..... Plt./289
CPC ..... A01H 6/1424; A01H 5/02
See application file for complete search history.

*Primary Examiner* — Keith O. Robinson
(74) *Attorney, Agent, or Firm* — Dale Skalla

(57) ABSTRACT

A new garden type *Chrysanthemum* plant named 'CIFZ0107' particularly distinguished by its medium size plant with oval plant habit, a medium size decorative flower with orange buds that open into a golden bronze flower with dark orange center, and a natural season response in early September.

1 Drawing Sheet

Figure 1:
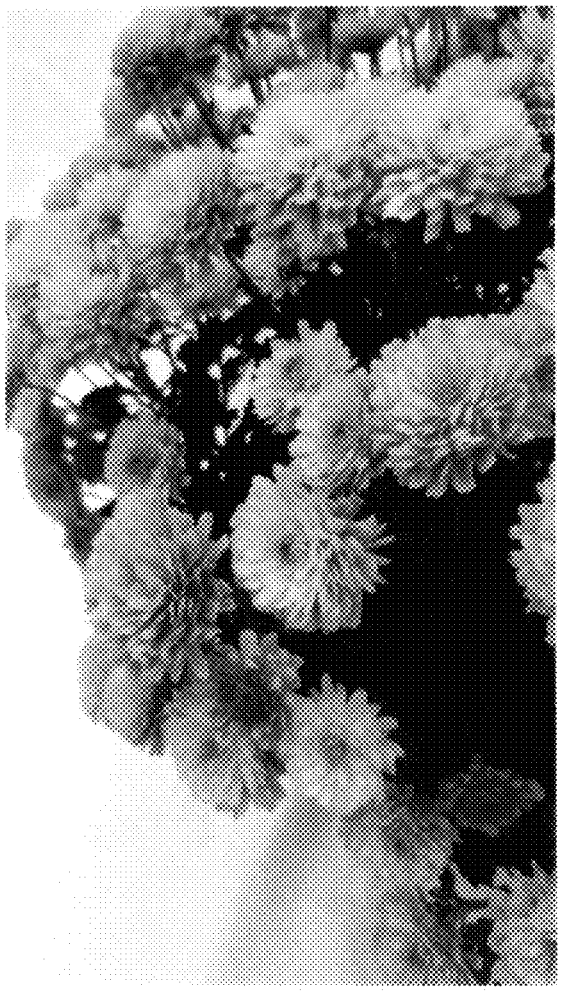

Latin name of the genus and species of the plant claimed: *Chrysanthemum* x *morifolium*.

Varietal denomination: 'CIFZ0107'.

BACKGROUND OF THE NEW PLANT

The present invention comprises a new *Chrysanthemum*, botanically known as *Chrysanthemum* x *morifolium*, and hereinafter referred to by the variety name 'CIFZ0107'.

'CIFZ0107' is a product of a planned breeding program. The new cultivar has medium size plant with oval plant habit, a medium size decorative flower with orange buds that open into a golden bronze flower with dark orange center, and a natural season response in early September.

'CIFZ0107' originated from a cross made in November 2018 in Enkhuizen, The Netherlands. Seeds were sown in June 2019 in Alva, Fla. and 'CIFZ0107' was selected from the resulting population on Oct. 14, 2019 in Alva, Fla.

The female parent was 'CIFZ0074', U.S. Plant Pat. No. 32,976.

TABLE 1

Characteristics of the female parent, compared to 'CIFZ0107':

| | 'CIFZ0107' | 'CIFZ0074' |
|---|---|---|
| Natural response: | ½ week slower | ½ week faster |
| Blackcloth response: | Similar | Similar |
| Flower size: | Bit larger | Bit smaller |
| Flower color: | Orange/Golden Bronze | Red |
| Flower type: | Similar | Similar |
| Plant size: | Similar | Similar |
| Plant habit: | Similar | Similar |
| Flower longevity: | Flowers last but color fades | Flowers and color hold up |
| Plant strength: | Similar | Similar |
| Flowering uniformity: | Similar | Similar |

The male parent is unknown as different males were grouped and sown together.

The first act of asexual reproduction of 'CIFZ0107' was accomplished when vegetative stem cuttings were propagated from the initial selection in January 2020 in Alva, Fla.

BRIEF SUMMARY OF INVENTION

Horticultural examination of plants grown from cuttings of the plant initiated in January 2020 and continuing thereafter, has demonstrated that the combination of characteristics as herein disclosed for 'CIFZ0107' are firmly fixed and are retained through successive generations of asexual reproduction.

'CIFZ0107' has not been observed under all possible environmental conditions. The phenotype may vary significantly with variations in environment such as temperature, light intensity and day length.

A Plant Breeder's Right for this cultivar has not yet been applied for. 'CIFZ0107' has not been made publicly available prior to the effective filing date of this application, notwithstanding any disclosure that may have been made less than one year prior to the effective filing date of this application by the inventor or another who obtained 'CIFZ0107' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0107' with colors being as true as possible with an illustration of this type.

Figure 2:
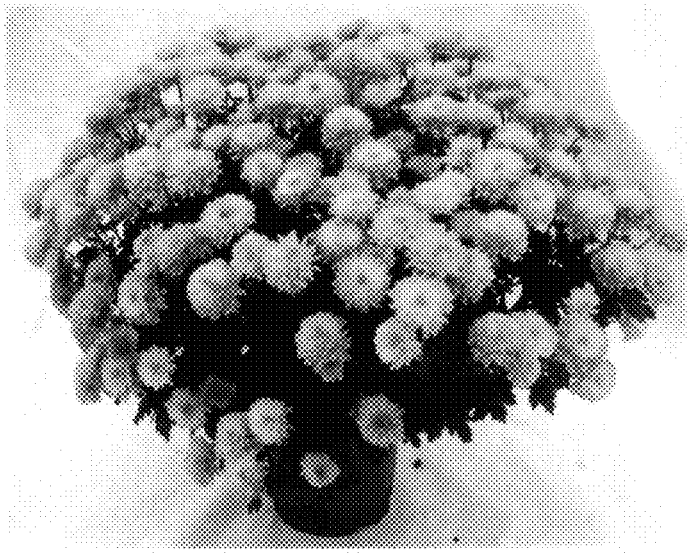

The photographic drawing shows in FIG. 1 a close view of flower of the new variety and in FIG. 2 a flowering plant from an outdoor trial.

The aforementioned photographs: FIG. 1, as well as FIG. 2, were taken on Sep. 5, 2022 both showing a plant from the same blackcloth indoor trial in Enkhuizen, The Netherlands.

These plants were about 13 weeks of age. One rooted cutting per pot had been planted in a 19 cm pot, not pinched in week 23, 2022 and black clothed from week 29. Plants started flowering the end of August 2022.

The measurements were taken in Enkhuizen, The Netherlands, in September 2022 on plants from the same indoor blackcloth trial.

DETAILED BOTANICAL DESCRIPTION

Color references are made to The Royal Horticultural Society Colour Chart (R.H.S.) 2001.

TABLE 2

DIFFERENCES BETWEEN THE NEW VARIETY 'CIFZ0107' AND TWO MOST SIMILAR VARIETIES:

| | 'CIFZ0107' | 'Syelect Ambe', U.S. Plant Pat. No. 22,770 |
|---|---|---|
| Natural response: | Approximately 1 week faster | Approximately 1 week slower |
| Blackcloth response: | ½ week faster | ½ week slower |
| Flower size: | Bit smaller | Bit larger |
| Flower color: | Darker bud color and more bicolor effect once flowers open | Ligher bud color and less bicolor effect once flowers open |
| Flower type: | Similar | Similar |
| Plant size: | Less width | More width |
| Plant habit: | Less round/ more oval | Rounder |
| Flower longevity: | More fade/20% less longevity | Less fade/20% more longevity |
| Flowering uniformity: | Less uniform | More uniform |

| | 'CIFZ0107' | 'Autumn Envy', Patent Application Applied For |
|---|---|---|
| Natural response: | Almost 1 week faster | Almost 1 week slower |
| Flower size: | Smaller | Larger |
| Flower color: | Similar | Similar |
| Flower type: | Similar | Similar |
| Plant size: | Larger overall | Smaller overall |
| Plant habit: | Taller than width | Similar height to width |
| Plant strength: | Sturdier/less splitting | Weaker/more splitting |
| Foliage: | Similar | Similar |
| Flowering uniformity: | Similar | Similar |

Plant:

*Form, growth and habit.*—Herbaceous garden-type, stems Upright and outwardly spreading, freely branching, medium vigorous growth habit.

*Plant height* (*above soil*).—25 cm.

*Plant height* (*inflorescence included*).—28 cm.

*Plant width.*—46 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 137A.

*Immature leaf, color lower surface.*—RHS 137C.

*Mature leaf, color, upper surface.*—RHS 137B.

*Mature leaf, color lower surface.*—RHS 137C.

*Length.*—4.0 cm.

*Width.*—3.5 cm.

*Shape.*—Ovate, with distinct lobes.

*Base shape.*—Shortly Attenuate.

*Apex shape.*—Acute.

*Margin.*—5 lobed (Palmate).

*Number of margin indentations.*—13 to 15.

*Depth of margin indentations.*—3 mm.

*Leaf length terminal lobe relative to total leaf length.*—1:2.2.

*Leaf depth lower lateral sinus.*—1.2 cm.

*Texture, upper surface.*—Bifid hairs.

*Texture, lower surface.*—Bifid hairs.

*Color of veins, upper surface.*—RHS 137C.

*Color of veins, lower surface.*—RHS 137C.

*Pattern of veining.*—Palmate.

*Petiole color.*—RHS 137C.

*Petiole length.*—1.4-1.8 cm.

*Diameter.*—0.2 cm.

*Texture.*—Bifid hairs.

*Presence of stipules.*—No.

Stem:

*Quantity of main branches per plant.*—6-7.

*Color of stem.*—RHS 146C.

*Length of stem.*—12.0-13.0 cm.

*Diameter.*—0.4 cm.

*Length of internodes.*—2.0-2.5 cm.

*Texture.*—Bifid hairs.

*Color of peduncle.*—RHS 146C.

*Length of peduncle.*—4.0-5.5 cm.

*Peduncle diameter.*—0.2 cm.

*Texture.*—Bifid hairs.

Inflorescence:

*Type.*—Compositae, solitary, decorative type inflorescences borne terminally above foliage, ligulate ray florets arranged in whorls on a capitulum giving a double flower.

*Quantity of short days to flowering* (*response time*).—Approximately 6.0 weeks.

*Quantity of inflorescences per plant.*—70-80 with several small buds developing.

*Lastingness of individual blooms on the plant.*—About six weeks from first color.

*Fragrance.*—Slightly spicy.

Bud (when showing color):

*Color.*—RHS 29B.

*Length.*—0.7 cm.

*Width.*—0.5 cm.

*Shape.*—Oblate.

Immature inflorescence (at moment of opening):

*Diameter.*—2.5 cm.

*Color of ray florets, upper surface.*—RHS 163B.

*Color of ray florets, lower surface.*—RHS 16B.

Mature inflorescence:
*Diameter.*—3.5 cm.
*Depth.*—1.5 cm.
*Total diameter of disc.*—0.0-0.5 cm.
*Receptacle color.*—RHS 148B.
*Receptacle height.*—0.3 cm.
*Receptacle diameter.*—1.1 cm.
*Length of corolla tube.*—0.1 cm.

Ray florets:
*Average quantity of florets.*—110-130.
*Color of florets, upper surface.*—RHS 9A.
*Color lower surface.*—RHS 22B.
*Length.*—1.4 cm.
*Width/diameter.*—0.3-0.4 cm.
*Shape.*—Elliptical.
*Apex shape.*—Dentate.
*Base shape.*—Tube.
*Margin.*—Entire — Small incisions may be present at tip.
*Margin.*—Type of rolling — Weakly involute.
*Texture, upper surface.*—Papillate.
*Lower surface.*—Papillate.
*Ribs present.*—Yes.
*Number of keels.*—1.
*Profile at widest point.*—Flat.
*Longitudinal axis shape.*—Straight, occasionally twisted.
*Longitudinal axis curvature strength.*—Medium.
*Corolla tube shape.*—Circular.

Disc florets:
*Number of disc florets.*—0-30.
*Width.*—0.1 cm.
*Length.*—1.0 cm.
*Color.*—RHS 14A.

Inflorescence (at moment of senescence):
*Color of ray florets, upper surface.*—RHS 11A.
*Color of ray florets, lower surface.*—RHS 163B.

Phyllaries:
*Quantity.*—18-22.
*Color, upper surface.*—RHS 148B.
*Color, lower surface.*—RHS 137B.
*Length.*—0.7 cm.
*Width.*—0.2 cm.
*Shape.*—Lanceolate.
*Apex shape.*—Acute.
*Base.*—Fused.
*Margins.*—Entire.
*Texture, upper surface.*—Glabrous.
*Texture, lower surface.*—Canescent.

Reproductive organs:
*Pistil.*—One.
*Length.*—0.4 cm.
*Style color.*—RHS 5C.
*Style length.*—0.3 cm.
*Stigma color.*—RHS 5C.
*Stigma shape.*—Bi-parted.
*Ovary color.*—RHS 157C.
*Ovary length.*—0.2 cm.
*Ovary width.*—0.1 cm.

Androecium:
*Stamens.*—1, found on only disc florets.
*Color of filaments.*—RHS 157C.
*Length filaments.*—0.2 cm.
*Anther color.*—RHS 15A.
*Anther length.*—0.2 cm.
*Anther shape.*—Oval to club shaped.
*Color of pollen.*—RHS 15A.
*Pollen amount.*—Moderate.
*Fertility/seed set.*—Has not been determined to date.
*Disease/pest resistance.*—Has not been determined to date.
*Hardiness.*—Has not been determined to date.

What is claimed is:

1. A new and distinct variety of *Chrysanthemum* plant named 'CIFZ0107' substantially as illustrated and described herein.

* * * * *